US008829229B2

(12) United States Patent
Tulchinsky et al.

(10) Patent No.: US 8,829,229 B2
(45) Date of Patent: Sep. 9, 2014

(54) POLYOL ETHERS AND PROCESS FOR MAKING THEM

(75) Inventors: Michael L. Tulchinsky, Midland, MI (US); John R. Briggs, Midland, MI (US); Cynthia L. Rand, Sanford, MI (US)

(73) Assignee: Dow Global Technologies LLC, Midland, MI (US)

( * ) Notice: Subject to any disclaimer, the term of this patent is extended or adjusted under 35 U.S.C. 154(b) by 425 days.

(21) Appl. No.: 12/543,751

(22) Filed: Aug. 19, 2009

(65) Prior Publication Data

US 2010/0048940 A1  Feb. 25, 2010

Related U.S. Application Data

(60) Provisional application No. 61/091,530, filed on Aug. 25, 2008.

(51) Int. Cl.
  *C07C 67/08*  (2006.01)
  *C07C 41/01*  (2006.01)
  *C07C 43/13*  (2006.01)
  *C07C 69/708*  (2006.01)
  *C07C 67/31*  (2006.01)

(52) U.S. Cl.
  CPC .............. *C07C 69/708* (2013.01); *C07C 41/01* (2013.01); *C07C 67/08* (2013.01); *C07C 67/31* (2013.01); *C07C 2101/14* (2013.01)
  USPC ........... 560/186; 568/626; 568/662; 568/670; 568/671; 568/679; 568/680

(58) Field of Classification Search
  None
  See application file for complete search history.

(56) References Cited

U.S. PATENT DOCUMENTS

| | | | |
|---|---|---|---|
| 2,932,670 A | 4/1960 | Blake et al. | |
| 3,170,958 A | 2/1965 | Howard et al. | |
| 4,088,700 A | 5/1978 | Watts, Jr. | |
| 4,479,017 A | 10/1984 | Ayusawa et al. | |
| 4,484,009 A | 11/1984 | Ghenassia et al. | |
| 5,446,208 A | 8/1995 | Koshino et al. | |
| 5,446,210 A | 8/1995 | Hees et al. | |
| 5,914,430 A | 6/1999 | Fujii et al. | |
| 6,011,071 A | 1/2000 | Fujii et al. | |
| 6,265,623 B1 | 7/2001 | Morawietz et al. | |
| 6,504,063 B2 | 1/2003 | Okutsu et al. | |
| 6,657,089 B1 | 12/2003 | Nagasawa et al. | |
| 6,753,290 B1 | 6/2004 | Romanenko et al. | |
| 2007/0129451 A1 | 6/2007 | Niemann | |
| 2008/0103340 A1 | 5/2008 | Binder et al. | |
| 2008/0293602 A1* | 11/2008 | Kodali | ........................ 508/463 |

FOREIGN PATENT DOCUMENTS

| | | |
|---|---|---|
| EP | 624563 | 11/1994 |
| GB | 1125730 | 8/1968 |

OTHER PUBLICATIONS

Fujii et al., "A Convenient Catalytic Method for the Synthesis of Ethers from Alcohols and Carbonyl Conpounds", Bull. Chem. Soc. Jpn., 2005, vol. 78, pp. 453-463, The Chemical Society of Japan.
Lemaire et al., "Reductive O- and N-alkylations. Alternative catalytic methods to nucleophilic substitution", Rec. Tray. Chim. Pays-Bas, 1996, pp. 231-238, vol. 115.
Bethmont et al., "An Alternative Catalytic Method to the Williamson's Synthesis of Ethers", Tetrahedron Letters, 1995, pp. 4235-4236, vol. 36 No. 24, Elsevier Science Ltd.
Bethmont et al., "Ether synthesis from alcohol and aldehyde in the presence of hydrogen and palladium deposited on charcoal", Journal of Molecular Catalysis A: Chemical, 2000, pp. 133-140, vol. 152.
Fache et al., "Reductive O- and N-alkylations. Alternative catalytic methods to nucleophilic substitution", Recueil des Travaux Chimiques des Pays-Bus, 1996, vol. 115, pp. 231-238.
Fujii et al., "A Convenient Catalytic Method for the Synthesis of Ethers from Alcohols and Carbonyl Compounds", Chemistry Letters, 2000, pp. 926-927, The Chemical Society of Japan.
Fujii et al., "A Convenient Catalytic Method for the Synthesis of Ethers from Alcohols and Carbonyl Conpounds", Bull. Chem. Soc. Jpn., 2005, vol. 78, pp. 456-463, The Chemical Society of Japan.
Gooßen et al., "Catalytic Reductive Etherification of Ketones with Alcohols at Ambient Hydrogen Pressure: A Practical, Waste-Minimized Synthesis of Dialkyl Ethers", Synlett, 2006, vol. 20, pp. 3489-3491.
Gu et al., "Heterogeneously catalyzed etherification of glycerol: new pathways for transformation of glycerol to more valuable chemicals", Green Chemistry, 2008, pp. 164-167, vol. 10, The Royal Society of Chemistry.
Hu et al., "Direct synthesis of palladium-containing mesoporous carbon", Microporous and Mesoporous Materials, 2005, vol. 81, pp. 149-154, Elsevier Inc.
International Search Report and Written Opinion for PCT/US2009/054277 dated Feb. 9, 2010.
Karinen et al., "New biocomponents from glycerol", Applied Catalysis A: General, 2006, pp. 128-133, vol. 306, Elsevier B.V.
Klepáčová et al., "tert-Butylation of glycerol catalysed by ion-exchange resins", Applied Catalysis A: General, 2005, pp. 141-147, vol. 294, Elsevier B.V.
Lemaire et al., "Reductive O- and N-alkylations. Alternative catalytic methods to nucleophilic substitution", Rec. Trav. Chin Pays-Bas, 1996, pp. 231-238, vol. 115.
Leofanti et al., "Surface area and pore texture of catalysts", Catalysis Today, 1998, vol. 41, pp. 207-219, Elsevier Science B.V.
Queste et al., "Short chain glycerol 1-monoethers-a new class of green solvo-surfactants", Green Chemistry, 2006, pp. 822-830, vol. 8, The Royal Society of Chemistry.
Rase, Chapter 12 "Hydrogenation", Handbook of Commercial Catalysts: Heterogeneous Catalysts, pp. 105-117, CRC Press, 2000.

(Continued)

*Primary Examiner* — Rosalynd Keys

(57) ABSTRACT

New polyol ether compounds and a process for their preparation. The process comprises reacting a polyol, a carbonyl compound, and hydrogen in the presence of hydrogenation catalyst, to provide the polyol ether. The molar ratio of polyol to carbonyl compound in the process is greater than 5:1.

16 Claims, No Drawings

(56) References Cited

OTHER PUBLICATIONS

Shi et al., "One-step selective synthesis of branched 1-O-alkyl-glycerol/diglycerol monoethers by catalytic reductive alkylation of ketones", Science China: Chemistry, 2010, vol. 53 No. 9, pp. 1953-1956, Science China Press and Springer-Verlag Berlin Heidelberg.

Shi et al., "Selective synthesis of 1-O-alkyl glycerol and diglycerol ethers by reductive alkylation of alcohols", Green Chemistry, 2010, 7 Pages, The Royal Society of Chemistry.

Shi et al., "Straightforward selective synthesis of linear 1-O-alkyl glycerol and di-glycerol monoethers", Tetrahedron Letters, 2009, vol. 50, pp. 6891-6893.

Tulchinsky et al., "One step, waste minimized synthesis of renewable glyceryl monoethers via catalytic reductive etherification", 2009, Abstract, ACS.

Verzele et al., "A General Synthesis of Ethers", J. Chem. Soc. 1963, 5598-5600.

Sallay, et al., Novel General Procedure for the Preparation of Homogeneous Nonionic Surfactants, Journal of Surfactants and Detergents, vol. 5, No. 4, p. 353-357, Oct. 2002.

\* cited by examiner

POLYOL ETHERS AND PROCESS FOR MAKING THEM

CROSS-REFERENCE TO RELATED APPLICATIONS

This application claims priority from U.S. provisional application Ser. No. 61/091,530, filed Aug. 25, 2008, which is incorporated herein by reference in its entirety.

FIELD OF THE INVENTION

The invention relates to a process for making polyol ethers by reacting a polyol with a carbonyl compound and hydrogen, in the presence of a catalyst. The invention also relates to new polyol ether compounds.

BACKGROUND OF THE INVENTION

Polyol ethers, such as glycerol ethers, glycol ethers and polyglycol ethers, are well established materials that find widespread use in industry and in consumer products, including as solvents, surfactants, wetting agents, emulsifying agents, lubricants, and intermediates for the preparation of surfactants.

Glycol and polyglycol ethers are typically produced by catalytic alkoxylation of glycols or polyglycols with alkylene oxides such as ethylene oxide. However, there are significant disadvantages to this process, including the difficulty of stopping the reaction after one molecule of alkylene oxide has added to one alcohol group of the glycol or polyglycol. Instead, it is typical for the reaction to continue proceeding, undesirably resulting in a molecular weight distribution of products.

The conventional preparation of glycerol mono-ethers, as an example of other polyols, is a three-step process requiring: (1) protecting glycerol with acetone to form solketal (4-hydroxymethyl-2,2-dimethyl-1,3-dioxolane), (2) reacting solketal with bromoalkanes in a strong alkali solution preferably in the presence of tetrabutylammonium bromide as a phase transfer catalyst, and (3) hydrolyzing the ketal protection with hydrochloric acid (see Queste et al, *Green Chem.* 2006, 8, 822-830). The process has several disadvantages, including that it involves three overall steps, generates large amounts of inorganic salts, and provides low product yields. Further, the process has not been demonstrated suitable for use with secondary alkyl bromides, thus limiting the structural diversity of potential products.

U.S. Pat. No. 5,446,210 describes a process for the production of polyol ethers by reacting a polyol and a carbonyl compound with hydrogen in the presence of a hydrogenation catalyst. A molar ratio of polyol to carbonyl compound of 5:1 to 1:5 is described, although a ratio of 1:1 to 1:4 is taught as preferred (also, all of the examples were conducted with an excess of carbonyl compound). One of the shortcomings of the '210 patent's process is the low yield of etherified polyols. For instance, the reference indicates total ether (mono and bis) yields of 35 to 50%. In addition to the low yields, the process exhibits low selectivity for the mono-ether product over the bis-ether product, as demonstrated in the reference's examples.

BRIEF SUMMARY OF THE INVENTION

The invention provides a process for making polyol ethers. The process comprises: reacting a polyol and a carbonyl compound with hydrogen in the presence of a hydrogenation catalyst to provide the polyol ether, wherein the molar ratio of the polyol to the carbonyl compound is greater than 5:1. The carbonyl compound is of the formula I:

$$R^1R^2C=O \qquad\qquad I$$

in which $R^1$ and $R^2$ are independently H, $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cylcoalkyl, or $R^1$ and $R^2$ together with the carbon to which they are attached form a $C_3$-$C_{12}$ cycloalkyl ring, and wherein the alkyl, alkenyl, aryl, and cycloalkyl groups of $R^1$ and $R^2$ are optionally substituted with 1, 2, or 3 groups independently selected from —OH, halogen, dialkylamino, and $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, and phenol.

The invention also provides novel polyol ether compounds.

DETAILED DESCRIPTION OF THE INVENTION

As noted above, the invention provides a process for making polyol ethers. The process exhibits several advantages over prior art methods. For instance, by using a large molar excess of polyol to carbonyl compound, the inventors have surprisingly observed an enhanced reaction rate, improved selectivity to the monoethers, and suppressed side-reactions, namely (1) carbonyl compound reduction to corresponding alcohols, (2) subsequent etherifications of remaining hydroxyl groups of the ether polyol to di-, tri-. and polyethers, (3) formation of symmetrical dialkyl ether byproducts from the alcohol generated in pathway (1) and the starting carbonyl compound. In addition, the process is a one step reaction that co-produces water as the only stoichiometric byproduct.

Further, where the process of the invention is carried out between a short-chain carbonyl compound of formula I that is relatively non-polar (e.g., where $R^1$ and $R^2$ are hydrogen and alkyl or both alkyl with a total number of carbons of five or less), and a highly polar polyol (e.g., polyols of formula II-5 discussed below), it has been observed by the inventors that such compounds generally form a single phase when mixed. The mutual miscibility of the two components is unexpected and allows for conducting the etherification reaction efficiently and optionally without a solvent (see the Examples).

The process of the invention is also advantaged over the prior art when the polyol is a glycol or polyglycol, because it permits for the formation of etherified compounds with a controlled number of alkoxy units in the molecule. The conventional process for preparing glycol and polyglycol ethers is through catalytic alkoxylation of alcohols with alkylene oxides, such as ethylene oxide. However, it is difficult to stop the conventional reaction after one molecule of alkylene oxide is added and the reaction therefore results in a broad distribution of products with different molecular weights. In contrast, the process of the invention results in uniform materials.

The process of the invention comprises reacting a polyol and a carbonyl compound with hydrogen in the presence of a hydrogenation catalyst. The molar ratio of polyol to carbonyl compound is greater than 5:1. The carbonyl compound is of the formula I:

$$R^1R^2C=O \qquad\qquad I$$

wherein $R^1$ and $R^2$ are independently H, $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cylcoalkyl, or $R^1$ and $R^2$ together with the carbon to which they are attached form a $C_3$-$C_{12}$ cycloalkyl ring, and wherein the alkyl, alkenyl, aryl, and cycloalkyl groups of $R^1$ and $R^2$ are optionally substituted with 1, 2, or 3 groups independently selected from —OH, halogen, dialkylamino, and $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, and phenol.

Preferred compounds of formula I, here designated as having formula I-1, include compounds in which $R^1$ and $R^2$ are independently H, $C_1$-$C_{22}$ alkyl, $C_2$-$C_{22}$ alkenyl, aryl-$C_1$-$C_{20}$ alkyl, aryl-$C_2$-$C_{20}$ alkenyl-, or $C_3$-$C_{12}$ cylcoalkyl, or $R^1$ and $R^2$ together with the carbon to which they are attached form a $C_3$-$C_{12}$ cycloalkyl ring, and wherein the alkyl, alkenyl, aryl, and cycloalkyl groups of $R^1$ and $R^2$ are optionally substituted with 1, 2, or 3 groups independently selected from —OH, halogen, dialkylamino, and $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, and phenol.

Preferred compounds of formula I and formula I-1, here designated as having formula I-2, include compounds in which at least one of $R^1$ and $R^2$ is not H. Also preferred are compounds where neither $R^1$ nor $R^2$ is H.

Preferred compounds of formulae I, I-1, and I-2, here designated as having formula I-3, include compounds in which $R^1$ is H, $C_1$-$C_{22}$ alkyl, or aralkyl-. More preferably, $R^1$ is H or $C_1$-$C_{22}$ alkyl. Further preferably, $R^1$ is $C_1$-$C_{12}$ alkyl or $C_1$-$C_6$ alkyl.

Preferred compounds of formulae I, I-1, I-2, and I-3, here designated as having formula I-4, include compounds in which $R^2$ is H, $C_1$-$C_{22}$ alkyl, or aralkyl-. More preferably, $R^2$ is H or $C_1$-$C_{22}$ alkyl. Further preferably, $R^2$ is $C_1$-$C_{12}$ alkyl or $C_1$-$C_6$ alkyl.

Preferred compounds of formulae I, I-1, I-2, I-3, and I-4, here designated as having formula I-5, also include compounds in which one of $R^1$ and $R^2$ is H and the other is $C_1$-$C_{22}$ alkyl, more preferably one of $R^1$ and $R^2$ is H and the other is $C_1$-$C_{14}$ alkyl.

Preferred compounds of formulae I, I-1, I-2, I-3, and I-4, here designated as having formula I-6, further include compounds in which $R^1$ and $R^2$ are independently $C_1$-$C_{22}$ alkyl, more preferably independently $C_1$-$C_{14}$ alkyl.

Suitable carbonyl compounds of formula I include: glutaraldehyde, formaldehyde, acetaldehyde, acrolein, propionaldehyde, butyraldehyde, crotonaldehyde, caproic aldehyde, caprylic aldehyde, capric aldehyde, lauryl aldehyde, myristyl aldehyde, cetyl aldehyde, stearyl aldehyde, oleyl aldehyde, elaidyl aldehyde, linolyl aldehyde, linolenyl aldehyde, behenyl aldehyde, erucyl aldehyde, isobutyraldehyde, n-butyraldehyde, methylethylketone, 2-undecanone, n-decanal, 2-methylundecanal, n-valeraldehyde, iso-valeraldehyde, n-hexanal, n-heptanal, 2-ethylhexanal, acetone, methylethylketone, 2-pentanone, 3-pentanone, cinnamaldehyde, levulinic acid, 1,3-cyclohexanedicarboxaldehyde, 1,4-cyclohexanedicarboxaldehyde, cyclohexanone, and mixtures of two or more thereof.

Preferred carbonyl compounds of formula I include: n-butyraldehyde, methylethylketone, 2-undecanone, n-decanal, 2-methylundecanal, n-valeraldehyde, iso-valeraldehyde, n-hexanal, n-heptanal, 2-ethylhexanal, acetone, methylethylketone, 2-pentanone, 3-pentanone, cinnamaldehyde, levulinic acid, 1,3-cyclohexanedicarboxaldehyde, 1,4-cyclohexanedicarboxaldehyde, cyclohexanone, and mixtures of two or more thereof. In one particular embodiment, the carbonyl compound is a mixture of 1,3-cyclohexanedicarboxaldehyde and 1,4-cyclohexanedicarboxaldehyde. In the case of unsaturated carbonyl compounds, the double bonds thereof may be hydrogenated during the reaction to form saturated moieties.

As noted, the invention encompasses carbonyl compounds that are additionally functionalized (compounds in which the alkyl, alkenyl, aryl, and cycloalkyl groups of $R^1$ and $R^2$ are substituted with 1, 2, or 3 groups independently selected from —OH, halogen, dialkylamino, and $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, and phenol). Such functionalities are capable of undergoing additional or tandem reaction to form further materials during the process of the invention.

For instance, where the functional group is carboxylic acid, such as in levulinic acid, the carboxylic acid moiety is capable of undergoing esterification in tandem with the etherification of the carbonyl portion of the molecule. The Examples provide further illustrations of this embodiment.

Carbonyl compounds are available from a variety of commercial sources and/or can be readily prepared by a person of ordinary skill in the art using well known techniques. The source of the carbonyl compound and its method of preparation are not critical to the invention. For instance, aldehydes derived from seed oils or other natural sources are encompassed, as well as aldehydes that are byproducts of industrial processes, or those derived from hydroformylation reactions.

The polyol used in the process of the invention is generally a compound that contains at least two hydroxyl groups. Preferred are polyols of the formula II:

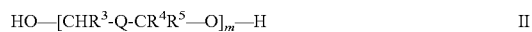

HO—[$CHR^3$-Q-$CR^4R^5$—O]$_m$—H    II wherein $R^3$ at each occurrence is independently H, $C_1$-$C_{20}$ alkyl, aralkyl-, or $C_3$-$C_{12}$ cycloalkyl;

$R^4$ and $R^5$ are independently at each occurrence selected from H, $C_1$-$C_{20}$ alkyl, aralkyl-, or $C_3$-$C_{12}$ cycloalkyl;

wherein the alkyl, aryl, and cycloalkyl groups of $R^3$, $R^4$, and $R^5$ are optionally substituted with 1, 2, or 3 groups independently selected from —OH, halogen, dialkylamino, $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, and phenol;

Q at each occurrence is independently a covalent bond or is a spacer group of the formula L, X, L-X, X-L, or L-X-L, wherein L is independently at each occurrence $C_1$-$C_{14}$ alkylene, $C_1$-$C_{14}$ heteroalkylene, or $C_2$-$C_{14}$ alkenylene, and X is $C_3$-$C_{12}$ cycloalkylene, heterocycloalkylene, arylene, or heteroarylene, wherein each alkylene, heteroalkylene, alkenylene, cycloalkylene, heterocycloalkylene, arylene and heteroarylene is optionally substituted with 1, 2, 3, or 4 groups independently selected from —OH, —$OCHR^1R^2$, halogen, dialkylamino, $C_1$-$C_6$ alkyl, hydroxylalkyl, and $C_1$-$C_6$ alkyl substituted with —$OCHR^1R^2$; and m is an integer from 1 to 2000, wherein the compound of formula II contains at least two hydroxy groups.

When m in the polyols of formula II is 2 or more, the groups within the m unit may be the same or different from one unit to another. For instance, if m is 2, $R^3$ in one unit may, for example, be H whereas $R^3$ in the other unit may, for example, be alkyl. It is preferred, however, that the groups be the same from one m unit to another.

Preferred polyols of formula II, here designated as having formula II-1, include compounds in which $R^3$ is H or $C_1$-$C_{20}$ alkyl. More preferably, $R^3$ is H.

Preferred polyols of formula II or II-1, here designated as having formula II-2, include compounds wherein at least one of $R^4$ and $R^5$ is H and the other is H or $C_1$-$C_{20}$ alkyl. Preferred alkyl for this embodiment are $C_1$-$C_{10}$ alkyl, more preferably $C_1$-$C_6$ alkyl, and even more preferably $C_1$-$C_4$ alkyl. Particularly preferred are methyl and ethyl.

Preferred polyols of formula II, II-1, or II-2, here designated as having formula II-3, include compounds wherein both $R^4$ and $R^5$ are H.

Preferred polyols of formula II, II-1, II-2, or II-3, here designated as having formula II-4, include compounds in which m is between 1 and 1000, more preferably between 1 and 500, and even more preferably, between 1 and 100. In some embodiments, m is between 1 and 10.

Preferred polyols of formulae II, II-1, II-2, II-3, or II-4, here designated as having formula II-5, include compounds where Q is a covalent bond or is $C_1$-$C_6$ alkylene. More preferably, Q is a covalent bond, or is a methylene or ethylene bridge.

In formula II-5, it is preferred that $R^3$ is H and $R^4$ and $R^5$ are independently H or $C_1$-$C_4$ alkyl. It is also preferred that m be between 1 and 20, more preferably between 1 and 10. Particularly preferred are compounds where m is 1, 2, 3, 4, 5, or 6. Preferred polyols according to formula II-5 include ethyleneglycol, diethyleneglycol, triethyleneglycol, tetraethyleneglycol, and polyethyleneglycols with different average molecular weight (e.g., number average molecular weights ranging from 62 to 620); 1,2-propyleneglycol; 1,3-propyleneglycol; 1,2-butyleneglycol; 1,3-butyleneglycol; 1,4-butyleneglycol, and mixtures thereof.

Preferred polyols of formulae II, II-1, II-2, II-3, or II-4, here designated as having formula II-6, also include compounds where Q is $C_1$-$C_{14}$ alkylene or $C_1$-$C_{14}$ heteroalkylene (preferably the heteroatom is oxygen, e.g., —$C_1$-$C_7$-alkyl-O—$C_1$-$C_7$ alkyl-). More preferably Q is $C_1$-$C_{10}$ alkylene, or even more preferably $C_1$-$C_6$ alkylene. The alkylene and heteroalkylene groups are optionally substituted with 1, 2, 3 or 4 hydroxy groups. Also preferred within this embodiment are polyols in which m is 1.

Preferred polyols according to embodiment II-6 are glycerol, sorbitol, mannitol, 2-hydroxymethyl-1,3-propanediol, 1,1,1-tris(hydroxymethyl)ethane, trimethylolpropane, pentaerythritol, diglycerol and mixtures thereof. By diglycerol is meant a compound selected from the following compounds, or a mixture of two or more thereof:

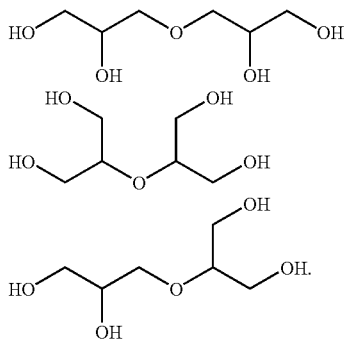

Polyols are available from a variety of commercial sources and/or can be readily prepared by a person of ordinary skill in the art using well known techniques. The source of the polyol is not critical to the invention. In some embodiments, obtaining the polyol from renewable non-petroleum sources, such as biobased feedstocks, is desirable. Bio-based polyols are described, for instance, in U.S. Pre-Grant Publication numbers 2007/0129451 and 2008/0103340, which are incorporated herein by reference.

The molar ratio of polyol to carbonyl compound in the process of the invention is greater than 5:1, thus providing a large excess of the polyol. As noted above, using a large molar excess of polyol, according to the invention, provides advantages over the prior art, including improved yields and product selectivity. In a preferred embodiment, the molar ratio of polyol to carbonyl compound is at least 6:1, or at least 7:1. Even more preferably it is at least 8:1 or at least 9:1. In a particularly preferred embodiment, the ratio is at least 10:1. There is no particular upper limit on the amount of excess polyol that is used, especially since the polyol can be recycled and reused. In some embodiments, it is preferred that the polyol to carbonyl compound molar ratio not exceed 100:1, more preferably not exceed 50:1.

In some embodiments, the process of the invention is conducted in the absence of strong acids or Lewis acids.

In a typical procedure, the polyol and the carbonyl compound are reacted with hydrogen in the presence of a hydrogenation catalyst. A solvent may be used, such as ether, dioxane, or THF. However, since the excess polyol itself functions as a solvent, additional solvent is not needed and is generally not preferred.

Suitable hydrogenation catalysts are well known in the art and include, by way of example, those that are based on Pd, Pt, Rh, or Ru as well as transition metals such as Ni, Co, Cu, and Fe. The catalyst loading (at 100% active) in the process preferably ranges from 0.001 to 3 weight percent, preferably from 0.01 to 1 weight percent, and more preferably from 0.3 to 0.8 weight percent, based on the weight of carbonyl compound. The catalyst may be present in a carrier such as carbon, alumina, silica gel or zeolites. A preferred catalyst/carrier is 10% Pd/C (pH of about 5), which is available from various commercial sources.

The reaction is carried out at a temperature of between 30 and 300° C., preferably at elevated temperature, such as between 100 and 250° C., more preferably between 150 and 220° C. Reaction pressure ranges from 0 to about 3000 psi. Elevated pressure is preferred, such as between 200 and 2000 psi and more preferably between 500 and 1500 psi.

Generally, the reaction is run from between a few minutes to about 24 hours, with 1 to 8 hours being preferred. The product(s) may be isolated from the reaction mixture by techniques well known to those skilled in the art, such as solvent extraction, distillation, and/or chromatography. For products that phase separate decantation may be used.

Preferred ether polyols prepared according to the process of the invention are of the formula III:

$$R^1R^2CHO-[CHR^3-Q-CR^4R^5-O]_m-H \qquad \text{III}$$

wherein $R^1$, $R^2$, $R^3$, $R^4$, $R^5$, Q, and m are as defined above for compounds of formula I and II, including the preferred embodiments thereof.

Preferred compounds of formula III are those in which at least one of $R^1$ and $R^2$ is not H. Also preferred are compounds where neither $R^1$ nor $R^2$ is H.

Preferred compounds also include those in which $R^1$ is H, $C_1$-$C_{22}$ alkyl, or aralkyl-. More preferably, $R^1$ is H or $C_1$-$C_{22}$ alkyl. Further preferably, $R^1$ is $C_1$-$C_{12}$ alkyl or $C_1$-$C_6$ alkyl.

Also preferred are compounds in which $R^2$ is H, $C_1$-$C_{22}$ alkyl, or aralkyl-. More preferably, $R^2$ is H or $C_1$-$C_{22}$ alkyl. Further preferably, $R^2$ is $C_1$-$C_{12}$ alkyl or $C_1$-$C_6$ alkyl.

Additionally preferred are compounds in which one of $R^1$ and $R^2$ is H and the other is $C_1$-$C_{22}$ alkyl, more preferably one of $R^1$ and $R^2$ is H and the other is $C_1$-$C_{14}$ alkyl.

Preferred compounds further include those in which $R^1$ and $R^2$ are independently $C_1$-$C_{22}$ alkyl, more preferably independently $C_1$-$C_{14}$ alkyl.

Further preferred are compounds in which $R^3$ is H or $C_1$-$C_{20}$ alkyl. More preferably, $R^3$ is H.

Also preferred are compounds wherein at least one of $R^4$ and $R^5$ is H and the other is H or $C_1$-$C_{20}$ alkyl. Preferred alkyl for this embodiment are $C_1$-$C_{10}$ alkyl, more preferably $C_1$-$C_6$ alkyl, and even more preferably $C_1$-$C_4$ alkyl. Particularly preferred are methyl and ethyl.

Additionally preferred are compounds in which m is between 1 and 1000, more preferably between 1 and 500, and even more preferably, between 1 and 100. In some embodiments, m is between 1 and 10.

Preferred compounds also include those where Q is a covalent bond or is $C_1$-$C_6$ alkylene. More preferably, Q is a covalent bond, or is a methylene or ethylene bridge. In this embodiment, it is also preferred that $R^3$ is H and $R^4$ and $R^5$ are independently H or $C_1$-$C_4$ alkyl. It is also preferred that m be between 1 and 20, more preferably between 1 and 10. Particularly preferred are compounds where m is 1, 2, 3, 4, 5, or 6.

Preferred compounds of formula III also include those in which Q is $C_1$-$C_{14}$ alkylene or $C_1$-$C_{14}$ heteroalkylene (preferably the heteroatom is oxygen, e.g., —$C_1$-$C_7$-alkyl-O—$C_1$-$C_7$ alkyl-). More preferably Q is $C_1$-$C_{10}$ alkylene, or even more preferably $C_1$-$C_6$ alkylene. The alkylene and heteroalkylene groups are optionally substituted with 1, 2, 3 or 4 substituents, with hydroxyl being a preferred substituent.

As noted above, where the carbonyl compound contains one or more additional functional groups, such functional groups are capable of undergoing further or tandem reaction during the process of the invention. For instance, a carboxylic acid functionality on the carbonyl compound may undergo esterification in tandem with the etherification of the carbonyl portion of the molecule.

Preferred polyol ethers prepared by the process of the invention are as follows:

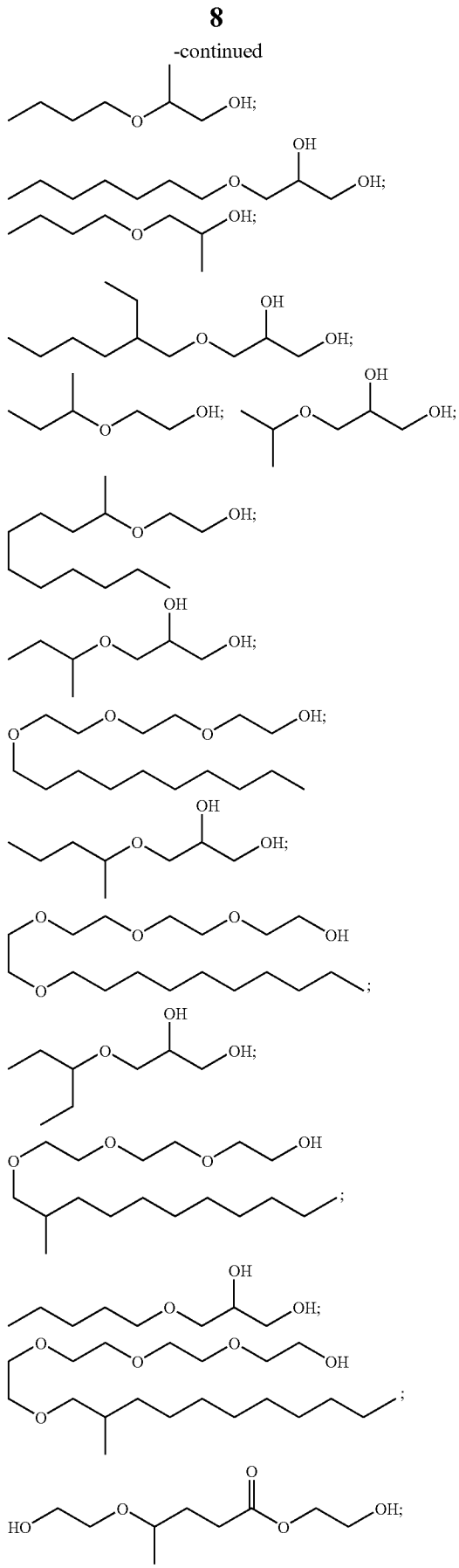

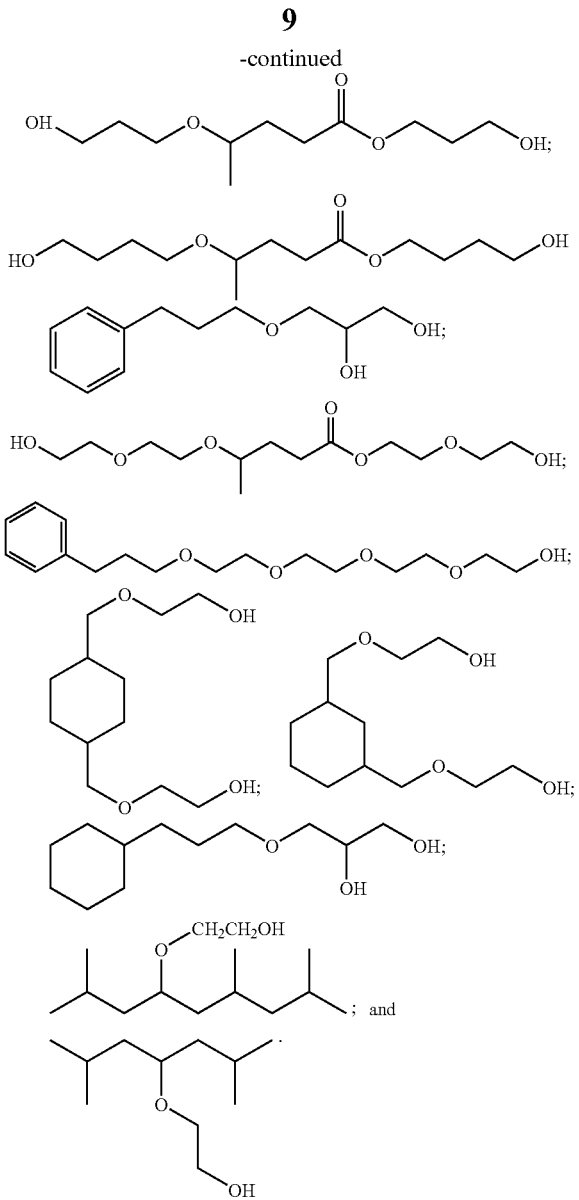

Some of the polyol ether compounds shown above are novel. Thus, in a further aspect, the invention provides compounds selected from:

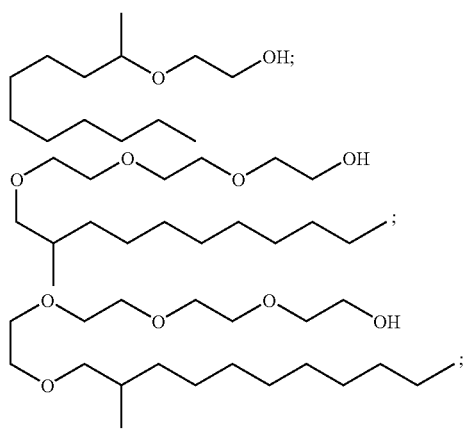

The ethers of the invention have wide ranging uses. Non-limiting examples of such uses include, for instance, as solvents, surfactants, degreasers, wetting agents, emulsifying agents, lubricants, and intermediates for surfactants. As such, the compounds are suitable for use in a large variety of applications including cleaning compositions, coatings, perfumery, inks, and for the solubilization of sparingly soluble compounds.

"Alkyl," as used in this specification, whether alone or as part of another group (e.g., in dialkylamino), encompasses straight and branched chain aliphatic groups having the indicated number of carbon atoms. If no number is indicated, alkyl preferably has 1-14 carbon atoms, more preferably 1-10 carbon atoms, and further preferably 1-6 carbon atoms. Preferred alkyl groups include, without limitation, methyl, ethyl, propyl, isopropyl, butyl, isobutyl, sec-butyl, tert-butyl, pentyl, hexyl, heptyl, octyl, nonyl, decyl, and undecyl.

The term "heteroalkyl" refers to an alkyl radical as defined above with one or more heteroatoms (nitrogen, oxygen, sulfur, phosphorus) replacing one or more carbon atoms within the radical. An example is an ether or a thioether.

The term "alkenyl" as used in this specification means an unsaturated straight or branched chain aliphatic group having the indicated number of carbon atoms and containing one or more carbon-carbon double bonds. If no carbon number is indicated, the group preferably contains 2-14 carbon atoms, more preferably 2-10 carbon atoms, and further preferably 2-6 carbon atoms. Preferred alkenyl groups include, without limitation, ethenyl, propenyl, butenyl, pentenyl, and hexenyl.

The term "alkynyl" as used herein means an unsaturated straight or branched chain aliphatic group having the indicated number of carbon atoms and containing one or more carbon-carbon triple bonds. If no carbon number is indicated, the group preferably contains 2-14 carbon atoms, more preferably 2-10 carbon atoms, and further preferably 2-6 carbon atoms.

The term "cycloalkyl" as employed herein includes saturated and partially unsaturated cyclic hydrocarbon groups having 3 to 12 carbons, preferably 3 to 8 carbons. Preferred cycloalkyl groups include, without limitation, cyclopropyl, cyclobutyl, cyclopentyl, cyclopentenyl, cyclohexyl, cyclohexenyl, cycloheptyl, and cyclooctyl.

"Heterocycloalkyl" refers to a non-aromatic 3-12 atom ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. A non-limiting example of a heterocycloalkyl group is tetrahydrofuran.

An "aryl" group is a $C_6$-$C_{12}$ aromatic moiety comprising one to three aromatic rings. Preferably, the aryl group is a $C_6$-$C_{10}$ aryl group. Preferred aryl groups include, without limitation, phenyl, naphthyl, anthracenyl, and fluorenyl. More preferred is phenyl. "Arylalkyl" or "aralkyl" refers to an aryl group attached to the parent molecular moiety through an alkyl group, as defined above.

"Heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, without limitation, pyridine and furan.

The terms "aralkyl-" and "aralkenyl-" refer, respectively, to aryl-$C_1$-$C_{20}$ alkyl- and aryl-$C_2$-$C_{20}$ alkenyl-.

The terms "alkylene," "heteroalkylene," "alkenylene," "cycloalkylene," "hyterocycloalkylene," "arylene," and "heteroarylene" correspond to the groups defined above but that are positioned between and serve to connect two other chemical groups. By way of example, alkylene groups include, without limitation, methylene, ethylene, propylene, and butylene. Arylene groups include, again without limitation, phenylene.

The following examples are illustrative of the invention but are not intended to limit its scope.

EXAMPLES

Examples 1-10 n-Butyraldehyde/Ethylene Glycol

In Examples 1-10, n-butyraldehyde, ethylene glycol, and hydrogen are reacted in the presence of Pd/C at various ratios and/or reaction conditions. The reaction procedure is generally as follows. The n-butyraldehyde, ethylene glycol, and Pd/C are charged to a Parr reactor. The system is purged with nitrogen three times. Then hydrogen is charged, the reactor is heated, and the hydrogen pressure is adjusted as necessary. Following the appropriate reaction time, the product mixture is analyzed by GC. Reaction conditions and GC results are summarized in Table 1.

TABLE 1

Conditions and results for 2-butoxyethanol preparation from n-butyraldehyde and ethylene glycol.

| Ex. | EG/BA molar ratio | 10% Pd/C wt % to BA | Temp ° C. | P, psi | Rxn time, hrs | Conv. of BA, GC % | 2-BE yield by GC, % | n-BuOH yield by GC, % | 1,2-DBE yield by GC, % | 2-PDO yield by GC, % |
|---|---|---|---|---|---|---|---|---|---|---|
| 1 | 20 | 5 | 180 | 1000 | 2 | 100 | 88.7 | 7.2 | 2.3 | 0 |
| 2 | 20 | 5 | 180 | 500 | 3 | 100 | 85.5 | 4.3 | 2.5 | 1.4 |
| 3 | 20 | 2.5 | 180 | 500 | 3 | 99.4 | 25.8 | 1.9 | 0.3 | 61.0 |
| 4 | 10 | 5 | 180 | 1000 | 2 | 100 | 83.4 | 8.3 | 4.2 | 0.7 |
| 5* | 5 | 5 | 180 | 1000 | 2 | 100 | 79.7 | 7.5 | 7.7 | 0.6 |
| 6 | 20 | 5 | 200 | 1000 | 2 | 100 | 87.7 | 5.2 | 2.1 | 0 |
| 7 | 20 | 5 | 160 | 1000 | 3 | 100 | 85.2 | 10.6 | 2.1 | 0.7 |
| 8 | 20 | 2.5 | 160 | 1000 | 2 | 99.8 | 47.8 | 6.3 | 5.8 | 44.3 |
| 9 | 20 | 5 | 140 | 1000 | 3 | 100 | 79.8 | 10.2 | 1.8 | 6.4 |
| 10 | 20 | 5 | 100 | 1000 | 8 | 100 | 76.5 | 13.1 | 1.8 | 7.1 |

EG = ethylene glycol;
BA = n-butyraldehyde;
2-BE = 2-butoxyethanol;
n-BuOH = 1-butanol;
1,2-DBE = 1,2-dibutoxyethane;
2-PDO = 2-propyl-1,3-dioxolane.
*Example 5 in Table 1 is comparative.

Comparative Example 1 n-Butyraldehyde/Ethylene Glycol: Two Step Synthesis

This example illustrates hydrogenolysis of 2-propyl-1,3-dioxolane, which is prepared in the Parr reactor from n-butyraldehyde and ethyleneglycol prior to hydrogenolysis.

n-Butyraldehyde (7.21 g, 9.01 ml, 0.1 mol), ethylene glycol (61.1 g, 55.8 ml, 1 mol), and 10% Pd/C (0.36 g, 5 wt % to n-butyraldehyde) are placed in a 150 ml Parr reactor and purged with nitrogen three times. Then the mixture is heated with stirring at 150° C. for 2 hours. GC analysis shows complete consumption of n-butyraldehyde and formation of 2-propyl-1,3-dioxolane along with some unidentified by-products with higher retention times. Hydrogen is charged, and the hydrogenolysis is carried out at 200° C. and 1000 psi for 2 hours. The resulting mixture contains 1% of remaining 2-propyl-1,3-dioxolane and only 61% of the desired 2-butoxyethanol.

Example 11 n-Butyraldehyde/Diethylene Glycol n-Butyraldehyde (3.6 g, 4.5 ml; 0.05 mol), diethylene glycol (106.1 g, 55.8 ml; 1 mol), and 0.18 g of 10% Pd/C are charged to a 150 ml Parr reactor. The system is purged with nitrogen three times. Then 500 psi of hydrogen is charged, the reactor is heated to 200° C., and set 1000 psi of hydrogen. After 2 hrs at 200° C. and 1000 psi, GC analysis shows complete consumption of n-butyraldehyde and formation of 3,6-dioxa-1-decanol (n-butyl carbitol) (94.5%), n-butanol (3.4%) and 2,2'-dibutoxy ethyl ether (2.1%).

Example 12 n-Butyraldehyde/Tetraethylene Glycol n-Butyraldehyde (1.8 g, 2.25 ml; 0.025 mol), tetraethylene glycol (97.1 g, 86.3 ml; 0.5 mol), and 0.09 g of 10% Pd/C are charged to a 150 ml Parr reactor. The system is purged with nitrogen three times. Then 500 psi of hydrogen is charged, the reactor is heated to 180° C., and set 1000 psi of hydrogen. After 4 hrs at 180° C. and 1000 psi n-butyraldehyde reacts completely, and GC analysis shows formation of 3,6,9,12-tetraoxahexadecanol (91.2%), n-butanol (4.8%) and 5,8,11,14,17-pentaoxauneicosane (1.1%).

Example 13 n-Butyraldehyde/Mixture of Glycols

This example illustrates reductive etherification of n-butyraldehyde with a mixture of glycols. n-Butyraldehyde (2.9 g, 3.6 ml; 0.04 mol), a mixture of ethyleneglycol (12.4 g, 11.2 ml, 0.2 mol), diethyleneglycol (21.2 g, 19.0 ml, 0.2 mol), triethyleneglycol (30.1 g, 26.7 ml, 0.2 mol), and tetraethylene glycol (38.9 g, 34.6 ml, 0.2 mol) and 0.15 g of 10% Pd/C are charged to a 150 ml Parr reactor. The system is purged with nitrogen three times. Then 500 psi of hydrogen is charged, the reactor is heated to 180° C., and set to 1000 psi of hydrogen. After 2 hrs at 180° C. and 1000 psi, n-butyraldehyde conversion reaches 98% GC analysis shows formation of monobutyl ethers of ethylene glycol, dietheylene glycol, triethylene glycol, and tetraethylene glycol along with 3-propyl-1,3-dioxolane and a small amount of n-butanol.

Example 14 n-Butyraldehyde/1,2-Propanediol n-Butyraldehyde (3.6 g, 4.5 ml; 0.05 mol), 1,2-propanediol (76.1 g, 73.4 ml; 1 mol), and 0.18 g of 10% Pd/C (5 wt % to n-butyraldehyde) are charged to a 150 ml Parr reactor. The system is purged with nitrogen three times. Then 500 psi of hydrogen is charged, the reactor is heated to 180° C., and the hydrogen pressure is adjusted to 1000 psi. After 3 hours at 180° C. and 1000 psi, GC analysis shows complete conversion of n-butyraldehyde and formation of an approximately 1:1 mixture of 2-butoxy-1-propanol and 1-butoxy-2-propanol (79.2%), n-butanol (5.8%), and cis/trans 2-propyl-4-methyl-1,3-dioxolane (11.9%).

Example 15

Methylethylketone/Ethylene Glycol

Methylethylketone (MEK, 3.6 g, 4.5 ml; 0.05 mol), ethylene glycol (62.1 g, 55.8 ml; 1 mol), and 0.2 g of 10% Pd/C are charged to a 150 ml Parr reactor. The system is purged with nitrogen three times. Then 500 psi of hydrogen is charged, the reactor is heated to 200° C., and the hydrogen pressure is adjusted to 1000 psi. After 3 hrs at 200° C. and 1000 psi, GC analysis shows 95% conversion of MEK and formation of 2-sec-butoxyethanol (84.7%), 2-methyl-2-ethyl-1,3-dioxolane (3.1%) and 1,2-di-sec-butoxyethane (2.8%).

Example 16

2-Undecanone/Ethylene Glycol

2-Undecanone (8.5 g, 10.3 ml; 0.05 mol), ethylene glycol (62.1 g, 55.8 ml; 1 mol), and 0.2 g of 10% Pd/C are charged in the Parr reactor. The system is purged with nitrogen three times. Then 500 psi of hydrogen is charged, the reactor is heated to 200° C., and the hydrogen pressure adjusted to 1000 psi. After 3 hrs at 200° C. and 1000 psi, GC analysis shows 98% conversion of 2-undecanone and formation of 2-sec-undecylethanol (87.1%), 2-undecanol (7.0%), and 2-methyl-2-nonyl-1,3-dioxolane (0.9%).

Comparative Example 2

2-Undecanone/Ethylene Glycol: Two-Step Synthesis

This example illustrates hydrogenolysis of 2-methyl-2-nonyl-1,3-dioxolane, which is prepared from 2-undecanone and ethyleneglycol and isolated prior to hydrogenolysis. A mixture of ethyleneglycol (12.4 g; 0.2 mol), 2-undecanone (17.3 g; 0.1 mol) and p-toluenesulfonic acid (1 g) in toluene (100 ml) is refluxed with a Dean-Stark trap for 3 hours. The reaction mixture is cooled and extracted with aqueous NaOH (50 ml×2), the toluene phase is dried over solid NaOH, then toluene is removed in vacuum and the crude product is distilled to give 18.7 g (87%) of 2-methyl-2-nonyl-1,3-dioxolane, 65-67° C./0.6 mm Hg. GC/MS: 199 (M-$CH_3$), 87, 43. NMR spectra are depicted in Figure 3.

Hydrogenolysis of 2-methyl-2-nonyl-1,3-dioxolane is conducted in hexane at 150° C. and 1000 psi of hydrogen for 2 hours using the procedure similar to the preceding Example. The dioxolane conversion after 2 hours is 99% and selectivity to 2-sec-undecylethanol is only 67%.

Example 17 n-Decanal/Triethylene Glycol n-Decanal (3.9 g, 4.7 ml, 0.025 mol), triethylene glycol (75.1 g, 66.8 ml, 0.5 mol) and 10% Pd/C (0.2 g, 5 wt % to n-decanal) are charged to a 150 ml Parr reactor. The system is purged with nitrogen three times. Then 500 psi of hydrogen is charged, the reactor is heated to 200° C., and the hydrogen pressure is adjusted to 1000 psi. After 3 hours at 200° C. and 1000 psi, GC analysis shows complete conversion of n-decanal and detects 3,6,9-trioxa-1-nonadecanol (82.6%) and n-decanol (13.7%).

Example 18 n-Decanal/Tetraethylene Glycol n-Decanal (3.9 g, 4.7 ml, 0.025 mol), tetraethylene glycol (97.1 g, 86.3 ml, 0.5 mol) and 10% Pd/C (0.2 g, 5 wt % to n-decanal) are charged to a 150 ml Parr reactor. The system is purged with nitrogen three times. Then 500 psi of hydrogen is charged, the reactor is heated to 200° C., and the hydrogen pressure is adjusted to 1000 psi. After 3 hours at 200° C. and 1000 psi, GC analysis shows complete conversion of n-decanal and detects 3,6,9,12-tetraoxa-1-docosanol (79.4%) and n-decanol (15.3%).

Example 19

2-Methylundecanal/Triethylene Glycol

2-Methylundecanal (4.61 g, 5.55 ml, 0.025 mol), triethylene glycol (75.1 g, 66.8 ml, 0.5 mol) and 10% Pd/C (0.3 g, 6.5 wt % to n-decanal) are charged to a 150 ml Parr reactor. The system is purged with nitrogen three times. Then 500 psi of hydrogen are charged, the reactor is heated to 200° C., and the hydrogen pressure is adjusted to 1000 psi. After 3 hours at 200° C. and 1000 psi, GC analysis shows 99.7% conversion of 2-methyl-undecanal and detects 11-methyl-3,6,9-trioxa-1-eicosanol (76.3%) and 2-methyundecanol (11.9%).

Example 20

2-Methylundecanal/Tetraethylene Glycol

2-Methylundecanal (4.61 g, 5.55 ml, 0.025 mol), tetraethylene glycol (97.1 g, 86.3 ml, 0.5 mol) and 10% Pd/C (0.3 g, 6.5 wt % to n-decanal) are charged to a 150 ml Parr reactor. The system is purged with nitrogen three times. Then 500 psi of hydrogen is charged, the reactor is heated to 200° C., and the hydrogen pressure is adjusted to 1000 psi. After 3 hours at 200° C. and 1000 psi, GC analysis shows 99.5% conversion of 2-methyl-undecanal and detect 11-methyl-3,6,9,12-tetraoxa-1-tricosanol (82.3%) and 2-methyundecanol (7.9%).

Example 21 n-Butyraldehyde/Glycerol n-Butyraldehyde (7.21 g, 8.96 ml, 0.1 mol), glycerol (92.09 g, 73.7 ml, 1 mol), and 10% Pd/C (5 wt %, 0.36 g) are charged to a Parr reactor, purged with nitrogen three times, heated to 200° C. with stirring and run at 1000 psi of hydrogen for 4 hrs. GC analysis shows complete consumption of n-butyraldehyde and formation of glycerol monoethers, 3-butyloxy-1,2-propanediol and 2-butoxy-1,2-propanediol, (83.1%, ratio 6.7), glycerol diethers 1,3-dibutoxy-2-propanol and 2,3-dibutoxy-1-propanol (7.1%), n-butanol (3.3%), di-n-butylether (0.3%).

Example 22 iso-Butyraldehyde/Glycerol iso-Butyraldehyde (7.21 g, 9.13 ml, 0.1 mol), glycerol (92.09 g, 73.7 ml, 1 mol), and 10% Pd/C (5 wt %, 0.36 g) are charged to the Parr reactor, purged with nitrogen three times, heated to 200° C. with stirring and run at 1000 psi of hydrogen for 8 hrs. GC analysis shows complete consumption of iso-butyraldehyde and formation of glycerol monoethers 3-iso-butyloxy-1,2-propanediol and 2-iso-butoxy-1,2-propanediol (80.1%, ratio 8.2), glycerol diethers 1,3-di-iso-butoxy-2-propanol and 2,3-di-iso-butoxy-1-propanol (7.1%), iso-butanol (2.7%).

Examples 23-25 n-Valeraldehyde/Glycerol

Examples 23-25 compare the effect of glycerol/aldehyde ratio on the monoether yield. The reaction conditions are as follows: 1000 psi hydrogen pressure, 200° C. reaction temperature, 8 hrs reaction time, 10% Pd/C catalyst at a 5 wt % catalyst loading. Results are summarized in Table 2.

TABLE 2

Effect of glycerol/valeraldehyde molar ratios on products yield.

| Ex. | Glycerol/valeraldehyde molar ratio | Valeraldehyde conversion | Monoether, % | Diether, % | Mono/di | Pentanol, % | Di-n-pentyl ether, % |
|---|---|---|---|---|---|---|---|
| 23 | 10 | 100 | 77.9 | 7.5 | 10.4 | 3.6 | 0.9 |
| 24* | 5 | 100 | 73.3 | 13.2 | 5.6 | 5.5 | 3.6 |
| 25* | 2 | 99.2 | 25.2 | 8.8 | 2.9 | 5.9 | 4.6 |

*Example 24 and 25 are comparative.

Example 26 iso-Valeraldehyde/Glycerol iso-Valeraldehyde (8.61 g, 10.8 ml, 0.1 mol), glycerol (92.09 g, 73.7 ml, 1 mol), and 10% Pd/C (5 wt %, 0.43 g) are charged to a Parr reactor, purged with nitrogen three times, heated to 200° C. with stirring and run at 1000 psi of hydrogen for 4 hrs. GC analysis shows complete consumption of iso-valeraldehyde and formation of glycerol monoethers 3-iso-pentoxy-1,2-propanediol and 2-isopentoxy-1,2-propanediol (82.0%, ratio 8.5), glycerol diethers 1,3-di-isopentoxy-2-propanol and 2,3-di-isopentoxy-1-propanol (8.4%), iso-pentanol (6.3%).

Example 27 n-Hexanal/Glycerol n-Hexanal (10.0 g, 12.3 ml, 0.1 mol), glycerol (92.09 g, 73.7 ml, 1 mol), and 10% Pd/C (5 wt %, 0.50 g) are charged to a Parr reactor, purged with nitrogen three times, heated to 200° C. with stirring and run at 1000 psi of hydrogen for 8 hrs. The reaction mixture forms two phases upon cooling. GC analysis of each phase shows complete consumption of n-hexanal. Bottom phase (glycerol): glycerol monoethers 3-hexoxy-1,2-propanediol and 2-hexoxy-1,2-propanediol (70.6%, ratio 7.8), glycerol diethers 1,3-dihexoxy-2-propanol and 2,3-dihexoxy-1-propanol (12.8%), n-hexanol (3.7%). Top phase (crude product): glycerol monoethers 3-hexoxy-1,2-propanediol and 2-hexoxy-1,2-propanediol (57.2%, ratio 8.4), glycerol diethers 1,3-dihexoxy-2-propanol and 2,3-dihexoxy-1-propanol (18.5%), n-hexanol (3.1%).

Example 28 n-Heptanal/Glycerol n-Heptanal (11.4 g, 14.0 ml, 0.1 mol), glycerol (92.09 g, 73.7 ml, 1 mol), and 10% Pd/C (5 wt %, 0.57 g) are charged to a Parr reactor, purged with nitrogen three times, heated to 200° C. with stirring and run at 1000 psi of hydrogen for 8 hrs. The reaction mixture forms two phases upon cooling. GC analysis of each phase shows complete consumption of n-heptanal. Bottom phase (glycerol): glycerol monoethers 3-heptoxy-1,2-propanediol and 2-heptoxy-1,2-propanediol (78.7%, ratio 7.7), glycerol diethers 1,3-diheptoxy-2-propanol and 2,3-diheptoxy-1-propanol (11.8%), n-heptanol (4.2%). Top phase (crude product): glycerol monoethers 3-heptoxy-1,2-propanediol and 2-heptoxy-1,2-propanediol (72.6%, ratio 7.9), glycerol diethers 1,3-diheptoxy-2-propanol and 2,3-diheptoxy-1-propanol (17.1%), n-heptanol (4.3%).

Example 29

2-Ethylhexanal/Glycerol

2-Ethylhexanal (12.8 g, 15.6 ml, 0.1 mol), glycerol (92.09 g, 73.7 ml, 1 mol), and 10% Pd/C (5 wt %, 0.64 g) are charged to a Parr reactor, purged with nitrogen three times, heated to 200° C. with stirring and run at 1000 psi of hydrogen for 7 hrs. The reaction mixture forms two phases upon cooling. GC analysis of each phase shows complete consumption of 2-ethylhexanal. Bottom phase (glycerol): glycerol monoethers 3-(2-ethyl)hexoxy-1,2-propanediol and 2-(2-ethyl)hexoxy-1,2-propanediol (55.4%, ratio 13.6), glycerol diethers 1,3-di(2-ethy)hexoxy-2-propanol and 2,3-di(2-ethyl)hexoxy-1-propanol (24.7%), 2-ethyhexanol (3.2%). Top phase (crude product): glycerol monoethers 3-di(2-ethyl)hexoxy-1,2-propanediol and 2-di(2-ethyl)hexoxy-1,2-propanediol (55%, ratio 12.8), glycerol diethers 1,3-di(2-ethy)hexoxy-2-propanol and 2,3-di(2-ethyl)hexoxy-1-propanol (24.8%), 2-ethylhexanol (3.5%).

Example 30

Acetone/Glycerol

Acetone (5.81 g, 7.34 ml, 0.1 mol), glycerol (92.09 g, 73.7 ml, 1 mol), and 10% Pd/C (5 wt %, 0.29 g) are charged to a Parr reactor, purged with nitrogen, heated to 200° C. with stirring and run at 1000 psi of hydrogen for 4 hrs. GC analysis reveals complete consumption of acetone and shows presence of glycerol monoether 3-isopropoxy-1,2-propanediol (78.5%), glycerol diethers 1,3-di-isopropoxy-2-propanol and 2,3-di-isopropoxy-1-propanol (3.9%), iso-propanol+acetone (7.2%).

Comparative Example

Hydrogenolysis of 2,2-dimethyl-4-hydroxymethyl-1,3-dioxolane 2,2-Dimethyl-4-hydroxymethyl-1,3-dioxolane (solketal) (19.8 g, 18.6 ml, 0.15 mol) and 10% Pd/C (5 wt %, 0.99 g) are charged to a Parr reactor, purged with nitrogen, heated to 200° C. with stirring and run at 1000 psi of hydrogen for 4 hrs. GC analysis reveals the presence of glycerol monoether 3-isopropoxy-1,2-propanediol (56.7%), glycerol diethers 1,3-di-isopropoxy-2-propanol and 2,3-di-isopropoxy-1-propanol (31.9%), glycerol (9.4%), iso-propanol (0.3%).

Example 31

Methylethylketone/Glycerol

Methylethylketone (7.21 g, 9.01 ml, 0.1 mol), glycerol (92.09 g, 73.7 ml, 1 mol), and 10% Pd/C (5 wt %, 0.36 g) are charged to a Parr reactor, purged with nitrogen, heated to 200° C. with stirring and run at 1000 psi of hydrogen for 7 hrs. GC analysis reveals complete consumption of methylethylketone and shows the presence of glycerol monoether, 3-sec-butoxy-1,2-propanediol and 2-sec-butoxy-1,3-propanediol (84.9%), glycerol diethers 1,3-di-sec-butoxy-2-propanol and 2,3-di-sec-butoxy-1-propanol (5.5%), 2-butanol (4.6%).

Example 32

2-Pentanone/Glycerol

2-Pentanone (8.61 g, 10.6 ml, 0.1 mol), glycerol (92.09 g, 73.7 ml, 1 mol), and 10% Pd/C (5 wt %, 0.43 g) are charged to a Parr reactor, purged with nitrogen, heated to 200° C. with stirring and run at 1000 psi of hydrogen for 4 hrs. GC analysis reveals 92% conversion of 2-pentanone and shows selectivity to 3-sec-pentoxy-1,2-propanediol and 2-sec-pentoxy-1,3-propanediol (76.2%, isomer ratio 32.1), 1,3-di-sec-pentoxy-2-propanol (6.1%), 2-pentanol (6.9%), 4-hydroxymethyl-2-methyl-2-propyl-1,3-dioxolane (cyclic ketal) (6.7%).

Example 33

3-Pentanone/Glycerol

3-Pentanone (8.61 g, 10.6 ml, 0.1 mol), glycerol (92.09 g, 73.7 ml, 1 mol), and 10% Pd/C (5 wt %, 0.43 g) are charged to a Parr reactor, purged with nitrogen, heated to 200° C. with stirring and run at 1000 psi of hydrogen for 9 hrs. GC analysis reveals 80.2% conversion of 3-pentanone and shows selectivity to 3-(3-pentoxy)-1,2-propanediol (40.7%), 1,3-di-(3-pentoxy)-2-propanol (0.5%), 4-hydroxymethyl-2,2-diethyl-2-1,3-dioxolane (cyclic ketal) (31.4%).

Example 34

Glycerol and Catalyst Recycling

The reaction in Example 23 is repeated, the reaction mixture is transferred from the Parr reactor to a separatory funnel without filtration and extracted with ether (50 ml×10). The glycerol phase (96.6 g) containing the catalyst is used for a second hydrogenolysis under identical conditions. After 6 hrs, GC analysis shows complete consumption of n-valeraldehyde and formation of glycerol monoethers, 3-pentoxy-1,2-propanediol and 2-pentoxy-1,2-propanediol, (64.3%), glycerol diethers (1,3-dipentoxy-2-propanol and 2,3-dipentoxy-1-propanol (5.2%), n-pentanol (18%), di-n-pentylether (0.9%).

Example 35

Levulinic Acid and Ethylene Glycol

Levulinic acid (8.7 g; 7.7 ml; 0.075 mol), anhydrous ethylene glycol (93.15 g, 83.7 ml; 1.5 mol), and 1.74 g of 10%

Pd/C from Aldrich (20 wt % relative to levulinic acid) are charged to a Parr reactor, purged with nitrogen three times, heated to 200° C. with stirring, and reacted with 1000 psi of hydrogen for 20 hrs. GC analysis reveals that the reaction is complete. The excess of ethylene glycol is evaporated at 0.2 mm Hg at 80° C. and the residue is chromatographed on silica gel using hexane-ethyl acetate from 3:1 to 1:2 to isolate 13.10 g of 2-hydroxyethyl 4-(2-hydroxyethoxy)pentanoate.

$^1$H NMR ($\delta$, ppm, CDCl$_3$): 1.09 d (3H, CH$_3$), 1.76 m (2H, CH$_2$), 2.38 m (2H, CH$_2$), 3.3-3.75 m (8H, CH$_2$O, OH, CH), 4.0-4.25 m (COOCH$_2$). $^{13}$C NMR ($\delta$, ppm, CDCl$_3$): 19.73 (CH$_3$); 31.12, 32.20 (CH$_2$CH$_2$); 60.81, 62.08, 66.22, 70.16 (OCH$_2$CH$_2$O), 75.42 (CH), 174.48 (COO). Mass spectrum: m/e 206 (M$^+$). The byproducts are identified as $\gamma$-valerolactone, 2-hydroxyethyl 3-(2-methyl-1,3-dioxolan-2-yl)propanoate, and 2-hydroxyethyl 4-oxopentanoate.

Example 36

Levulinic Acid and 1,3-Propanediol

Levulinic acid (11.6 g; 0.1 mol), 1,3-propanediol (67.6 g; 0.89 mol), and 2.32 g of 10% Pd/C from Aldrich (20 wt % relative to levulinic acid) are charged to a Parr reactor, purged with nitrogen three times, heated to 200° C. with stirring, and reacted with 1000 psi of hydrogen for 20 hrs. GC analysis reveals that the reaction is complete. 1,3-Propylene glycol is distilled off at 58-59° C./0.1 mm to give 14.7 g of the crude product containing 79% of the desired monomer. The crude product (1.0 g) is chromatographed on silica gel using hexane-ethyl acetate from 3:1 to 1:1 to isolate about 0.62 g of 3-hydroxypropyl 4-(3-hydroxypropoxy)pentanoate. $^1$H NMR ($\delta$, ppm, CDCl$_3$): 1.07 d (3H, CH$_3$), 1.66-1.80 m (6H, CH$_2$), 2.31 m (2H, CH$_2$CO), 3.1 (broad, 2H, OH), 3.39 m (2H, CH$_2$O), 3.57 m (5H, 2×CH$_2$OH, CH), 4.11 m (2H, COOCH$_2$). $^{13}$C NMR ($\delta$, ppm, CDCl$_3$): 19.69 (CH$_3$); 30.67, 31.85, 31.88; 32.68 (CH$_2$ groups); 59.02, 61.21, 61.70, 67.06 (CH$_2$O groups), 74.97 (CH), 174.15 (COO). Mass spectrum: m/e 234 (M$^+$).

Example 37

Levulinic Acid and 1,4-Butanediol

Levulinic acid (11.6 g; 0.1 mol), 1,4-butanediol (81.1 g; 0.9 mol), and 2.32 g of 10% Pd/C from Aldrich (20 wt % relative to levulinic acid) are charged to a Parr reactor, purged with nitrogen three times, heated to 230° C. with stirring, and reacted with 1000 psi of hydrogen for 16 hrs. GC analysis reveals that the reaction is complete. 1,4-Butanediol is distilled off at 75-80° C./0.1 mm to give 19.1 g of the crude product. A portion of this crude product is chromatographed on silica gel using methylene chloride-ethanol 12:1 to prepare an analytical sample of 4-hydroxybutyl 4-(4-hydroxybutoxy)pentanoate. $^1$H NMR ($\delta$, ppm, CDCl$_3$): 1.12 d (3H, CH$_3$), 1.62-1.80 m (10H, CH$_2$), 2.36 t (2H, CH$_2$CO), 2.0-2.6 (broad, 2H, OH), 3.42 m (3H, CH$_2$O, CH), 3.63 m (4H, 2×CH$_2$OH), 4.08 m (2H, COOCH$_2$). $^{13}$C NMR ($\delta$, ppm, CDCl$_3$): 19.46 (CH$_3$); 25.17; 27.02; 29.22; 30.18; 30.39; 31.61 (CH$_2$ groups); 62.18; 62.59; 64.21; 68.40 (CH$_2$O groups), 74.48 (CH), 173.56 (COO). Mass spectrum: m/e 262 (M$^+$).

Examples 38

Levulinic Acid and Dietheylene Glycol

Levulinic acid (11.6 g; 0.1 mol), diethylene glycol (63.6 g; 0.6 mol), and 2.32 g of 10% Pd/C from Aldrich (20 wt % relative to levulinic acid) are charged to a Parr reactor, purged with nitrogen three times, heated to 230° C. with stirring, and reacted with 1000 psi of hydrogen for 65 hrs. GC analysis reveals that the reaction is complete. Diethylene glycol is distilled off at 70-72° C./0.06 mm to give 15.6 g of the crude product, which is chromatographed on silica gel using at first neat methylene chloride and then methylene chloride-methanol from 30:1 to isolate 6.9 g of 2-(2-hydroxyethoxy)ethyl 4-(2-(2-hydroxyethoxy)ethoxy)pentanoate. $^1$H NMR ($\delta$, ppm, CDCl$_3$): 1.16 d (3H, CH$_3$), 1.81 m (2H, CH$_2$), 2.46 m (2H, CH$_2$CO), 3.1 (broad, 2H, OH), 3.50 m (3H, CH$_2$O, CH), 3.61 m (14H, 7CH$_2$O), 4.25 m (2H, COOCH$_2$). $^{13}$C NMR ($\delta$, ppm, CDCl$_3$): 19.30 (CH$_3$); 30.01; 31.27 (CH$_2$ groups); 61.38; 61.54; 63.22; 67.64; 68.88; 70.48; 72.33; 72.37 (CH$_2$O groups), 74.68 (CH), 173.57 (COO). Mass spectrum: m/e 294 (M$^+$).

Example 39

Renewable Carbonyl Compound and Tetra(ethylene glycol)

Trans-Cinnamaldehyde (3.30 g; 3.15 ml; 0.025 mol), tetra (ethylene glycol) (97.1 g; 86.3 ml; 0.5 mol) and 0.17 g of 10% Pd/C (5 wt % relative to the aldehyde) are charged to a Parr reactor, purged with nitrogen three times, heated to 200° C. with stirring and reacted at 1000 psi of hydrogen for 20 hrs. GC analysis reveals complete conversion of the aldehyde and formation of a new peak with higher retention time. The mixture is diluted with water (1:1), extracted with ether (50 ml×10), and dried over sodium sulfate. Then ether is evaporated to provide 6.35 g of the crude product, which is chromatographed on silica gel using hexane-ethyl acetate from 7:3 to 1:1. The yield of the pure product (structure below) is 3.55 g. The product is characterized by $^1$H and $^{13}$C NMR.

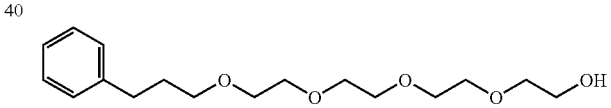

Example 40

Glyceryl Ether from Renewable Materials

Trans-Cinnamaldehyde (13.2 g, 12.6 ml, 0.1 mol) of, glycerol (92.09 g, 73.7 ml, 1 mol) and 10% Pd/C (0.66 g, 5 wt % relative to the aldehyde) are charged to a Parr reactor, purged three times with nitrogen, heated to 200° C. with stirring and reacted at 1000 psi of hydrogen for 20 h. GC analysis shows complete consumption of the aldehyde. The mixture is filtered, the product extracted with ether (50 ml×5), and the combined ether solution is dried with sodium sulfate. The solvent is evaporated and the residue chromatographed on silica gel using hexane-ethyl acetate from 5:1 to 1:1 to give 4.6 g of the monoether (95% purity). This product is approximately a 2:1 mixture of 3-(3-phenylpropyl)-1,2-propanediol and 3-(3-cyclohexylpropyl)-1,2-propanediol. The individual components of this mixture are separated by second column chromatography and characterized by $^1$H and $^{13}$C NMR.

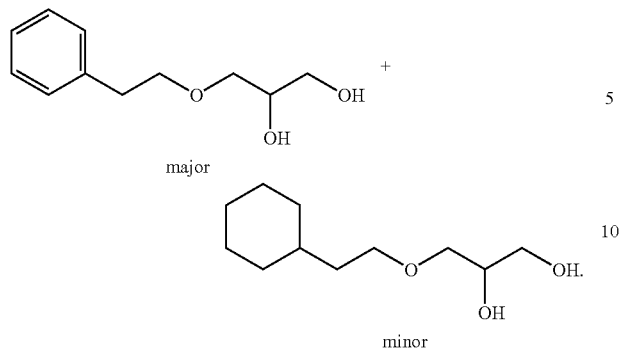

major minor

Example 41

Dialdehyde and Ethylene Glycol

An about 1:1 mixture of 1,3- and 1,4-dicyclohexanedicarboxaldehyde (7.0 g; 0.05 mol), ethylene glycol (62.1 g; 1 mol) and 0.35 g of 10% Pd/C (5 wt % relative to the dialdehyde) are charged to a Parr reactor, purged with nitrogen, heated to 200° C. at stirring and reacted with hydrogen for 4 hrs at 200° C. and 1000 psi. GC analysis shows complete consumption of the dialdehyde and formation of products. The mixture is filtered, the solution extracted with ether (50 ml×10), and the combined ether solution dried with sodium sulfate. The solvent is evaporated and the residue (13.2 g) chromatographed on silica gel using hexane-ethyl acetate 5:1 to give the product (as 4 isomers).

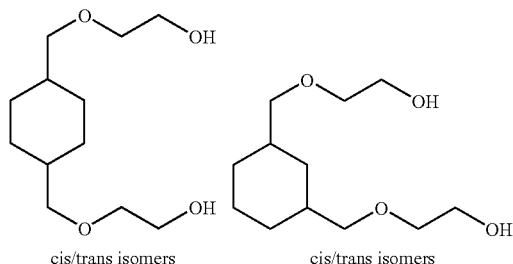

cis/trans isomers     cis/trans isomers

Example 42

Sterically Crowded 2,6-Dimethyl-4-heptanone with Ethylene Glycol 2,6-Dimethyl-4-heptanone (7.11 g; 0.05 mol), ethylene glycol (62.1 g; 1 mol), and 0.36 g of 10% Pd/C (5 wt % relative to the ketone) are charged in a Parr reactor, purged with nitrogen, heated to 200° C. with stirring and reacted with 1000 psi of hydrogen for 22 hrs. GC analysis reveals that approximately 50% of the ketone reacts. The top phase is separated, and the bottom phase is extracted with ether (50 ml×5). The ether solution is dried with sodium sulfate, and the solvent evaporated to give a crude product, which is chromatographed on silica gel using hexane-ethyl acetate 10:1. The purified product characterized by NMR:

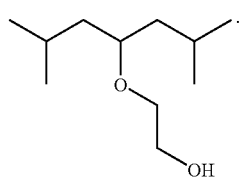

Example 43

Sterically Crowded 2,6,8-Trimethyl-4-nonanone with Ethylene Glycol 2,6,8-Trimethyl-4-nonanone (4.61 g; 0.025 mol), ethylene glycol (31.0 g; 0.5 mol) and 0.92 g of 10% Pd/C (20 wt % relative to the ketone) are charged in a Parr reactor, purged with nitrogen, heated to 200° C. with stirring and reacted at 1000 psi of hydrogen for 20 hrs. GC analysis reveals 74% ketone conversion. Water is added (1:1) and the system extracted with ether (50 ml×3). The combined ether solution is dried with sodium sulfate, the solvent is evaporated, the residue chromatographed on silica gel using hexane-ethyl acetate 9:1. The purified product is characterized by NMR:

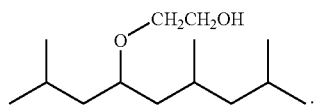

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for making a polyol ether, the process comprising:
reacting a polyol and a carbonyl compound with hydrogen in the presence of a hydrogenation catalyst at a pressure in a range of 500-1000 pounds per square inch to provide the polyol ether, wherein the molar ratio of the polyol to the carbonyl compound is greater than 5:1 and wherein the carbonyl compound is of the formula I:

$$R^1R^2C\!\!=\!\!O \qquad \qquad I$$

in which $R^1$ and $R^2$ are independently H, $C_1$-$C_{50}$ alkyl, $C_2$-$C_{50}$ alkenyl, aryl-$C_1$-$C_{50}$ alkyl, aryl-$C_2$-$C_{50}$ alkenyl-, or $C_3$-$C_{12}$ cylcoalkyl, or $R^1$ and $R^2$ together with the carbon to which they are attached form a $C_3$-$C_{12}$ cycloalkyl ring, and wherein the alkyl, alkenyl, aryl, and cycloalkyl groups of $R^1$ and $R^2$ are optionally substituted with 1, 2, or 3 groups independently selected from —OH, halogen, dialkylamino, and $C_1$-$C_6$ alkyl, aldehyde, ketone, carboxylic acid, ester, ether, alkynyl, dialkylamide, anhydride, carbonate, epoxide, lactone, lactam, phosphine, silyl, thioether, thiol, and phenol,
wherein a step to remove produced water during the process is excluded from the process, the process is conducted in the absence of strong acids or Lewis acids, and wherein the process is further characterized by producing greater than 50 percent yield of a combination of polyol mono and bis ethers based on total reaction products.

2. A process according to claim 1 wherein the molar ratio of the polyol to the carbonyl compound is at least 7:1.

3. A process according to claim 1 wherein the polyol is a compound of formula II:

HO—[CHR$^3$-Q-CR$^4$R$^5$—O]$_m$—H   II wherein R$^3$ at each occurrence is independently H, C$_1$-C$_{20}$ alkyl, aralkyl-, or C$_3$-C$_{12}$ cycloalkyl;
R$^4$ and R$^5$ are independently at each occurrence selected from H, C$_1$-C$_{20}$ alkyl, aralkyl-, or C$_3$-C$_{12}$ cycloalkyl;
wherein the alkyl, aryl, and cycloalkyl groups of R$^3$, R$^4$, and R$^5$ are optionally substituted with 1, 2, or 3 groups independently selected from —OH, halogen, amino, C$_1$-C$_6$ alkyl, aldehyde, ketone, carboxylic acid, ester, ether, alkynyl, dialkylamide, anhydride, carbonate, epoxide, lactone, lactam, phosphine, silyl, thioether, thiol, and phenol;
Q at each occurrence is independently a covalent bond or is a spacer group of the formula L, X, L-X, X-L, or L-X-L, wherein L is independently at each occurrence C$_1$-C$_{14}$ alkylene, C$_1$-C$_{14}$ heteroalkylene, or C$_2$-C$_{14}$ alkenylene, and X is C$_3$-C$_{12}$ cycloalkylene, heterocycloalkylene, arylene, or heteroarylene,
wherein each alkylene, heteroalkylene, alkenylene, cycloalkylene, heterocycloalkylene, arylene and heteroarylene is optionally substituted with 1, 2, 3, or 4 groups independently selected from —OH, —OCHR$^1$R$^2$, halogen, C$_1$-C$_6$ alkyl, hydroxylalkyl, and C$_1$-C$_6$ alkyl substituted with —OCHR$^1$R$^2$; and
m is an integer from 1 to 2000,
wherein the compound of formula II contains at least two hydroxy groups.

4. A process according to claim 3 wherein the polyol ether is of the formula III:

R$^1$R$^2$CHO—[CHR$^3$-Q-CR$^4$R$^5$—O]$_m$—H   III.

5. A process according to claim 3 wherein at least one of R$^1$ and R$^2$ is not H.

6. A process according to claim 3 wherein R$^1$ and R$^2$ are independently selected from H, C$_1$-C$_{22}$ alkyl, and aryl-C$_1$-C$_{50}$ alkyl.

7. A process according to claim 3 wherein R$^3$ is H or C$_1$-C$_{20}$ alkyl.

8. A process according to claim 3 wherein at least one of R$^4$ and R$^5$ is H and the other is H or C$_1$-C$_{20}$ alkyl.

9. A process according to claim 3 wherein Q is a covalent bond.

10. A process according to claim 3 wherein Q is C$_1$-C$_{14}$ alkylene or C$_1$-C$_{14}$ heteroalkylene, wherein the alkylene and heteroalkylene groups are optionally substituted with 1, 2, 3 or 4 hydroxy groups.

11. A process according to claim 3 wherein m is an integer from 1 to 100.

12. A process according to claim 1 wherein the polyol ether is of the following formula:

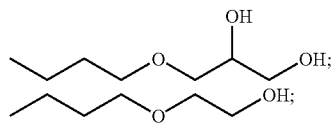

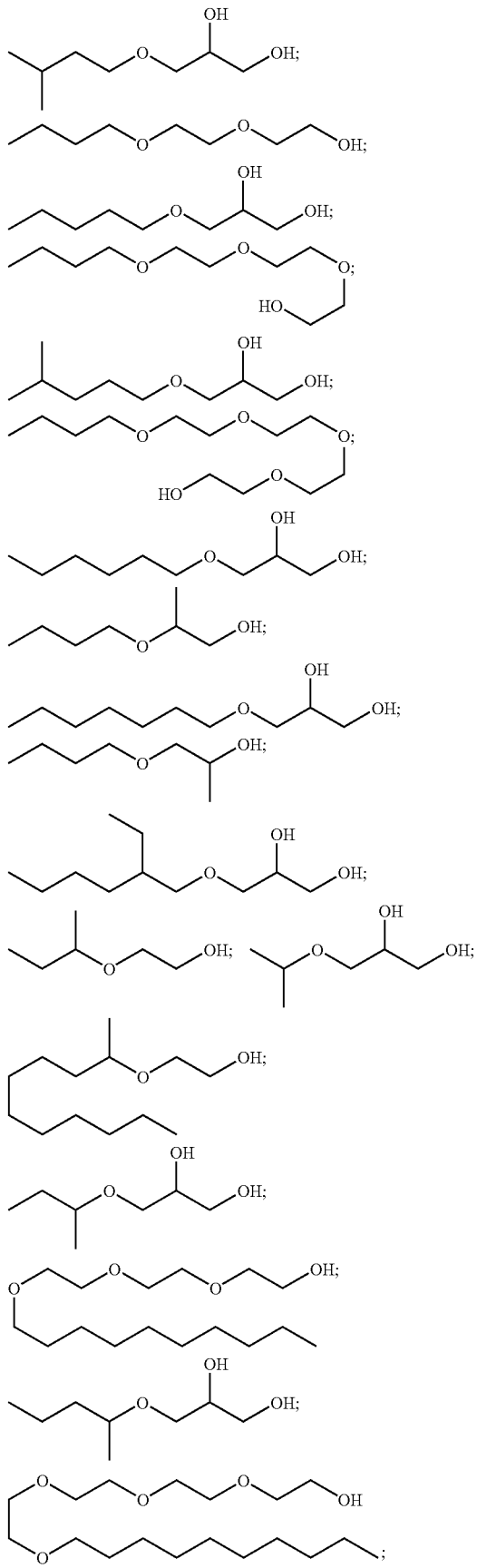

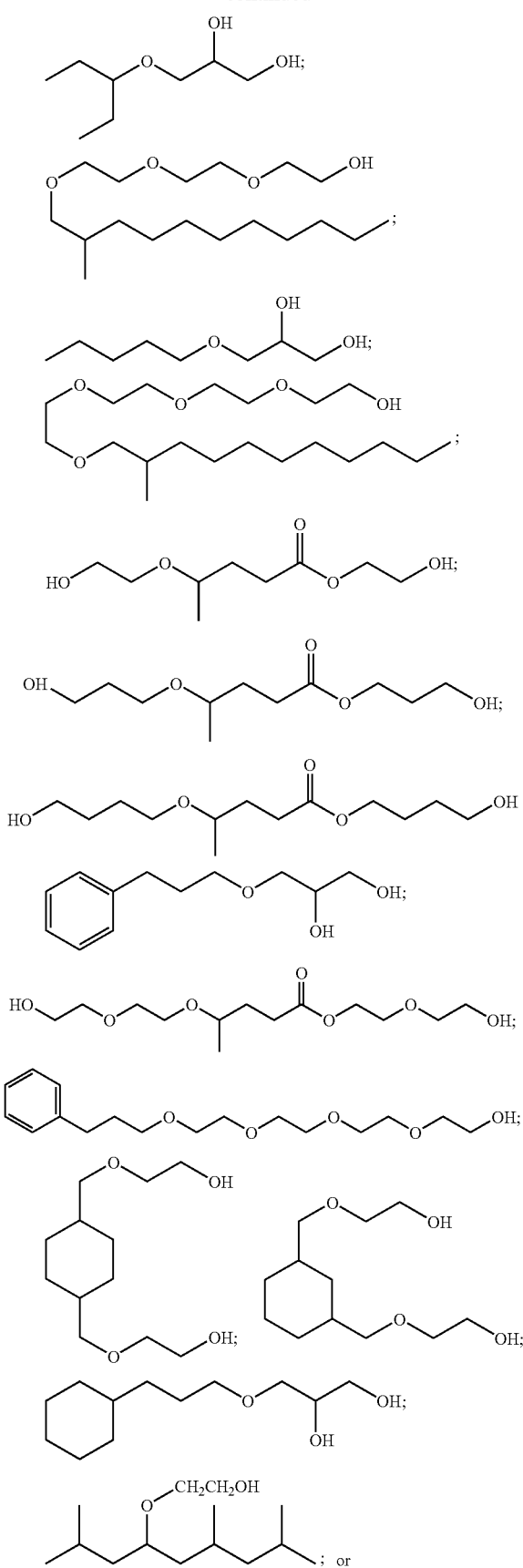
13. A process according to claim 1 wherein the polyol is obtained from a renewable, non-petroleum based, source.
14. A compound selected from:

15. The process of claim 1, where the process is further characterized by yielding at least 80% polyol monoether based on total reaction products.

16. The process of claim 1, where the process is further characterized by the polyol being glycerol.

* * * * *